(12) United States Patent
Beumer et al.

(10) Patent No.: US 8,874,399 B2
(45) Date of Patent: Oct. 28, 2014

(54) METHOD, COMPUTER PROGRAM, AND APPARATUS FOR DETECTING PIPETTING ERRORS

(75) Inventors: Thomas Beumer, Oss (NL); Bas Fleskens, Eindhoven (NL)

(73) Assignee: bioMérieux S.A., Marcy l'Etoile (FR)

( * ) Notice: Subject to any disclaimer, the term of this patent is extended or adjusted under 35 U.S.C. 154(b) by 0 days.

(21) Appl. No.: 13/497,724

(22) PCT Filed: Sep. 27, 2010

(86) PCT No.: PCT/EP2010/064235
§ 371 (c)(1),
(2), (4) Date: Apr. 19, 2012

(87) PCT Pub. No.: WO2011/036286
PCT Pub. Date: Mar. 31, 2011

(65) Prior Publication Data
US 2013/0073243 A1    Mar. 21, 2013

(30) Foreign Application Priority Data
Sep. 25, 2009    (EP) .................................... 09171349

(51) Int. Cl.
*G01F 1/12* (2006.01)
*G01N 35/10* (2006.01)

(52) U.S. Cl.
CPC .... G01N 35/1016 (2013.01); *G01N 2035/1018* (2013.01)
USPC ............. 702/100; 702/155; 702/98; 702/138; 702/140; 73/1.74; 73/861

(58) Field of Classification Search
USPC .............. 702/100, 155, 98, 138, 140; 73/861, 73/1.74
See application file for complete search history.

(56) References Cited

U.S. PATENT DOCUMENTS

| 5,814,275 A | 9/1998 | Lewis et al. |
| 6,094,966 A * | 8/2000 | Papen et al. ..................... 73/1.74 |

(Continued)

FOREIGN PATENT DOCUMENTS

| EP | 0726466 | 8/1996 |
| WO | WO 01/88549 | 11/2001 |

OTHER PUBLICATIONS

International Search Report and Written Opinion for corresponding PCT application No. PCT/EP2010/064235, Mail Date Sep. 30, 2011.

*Primary Examiner* — Hyun Park
(74) *Attorney, Agent, or Firm* — Myers, Bigel Sibley & Sajovec, P.A.

(57) ABSTRACT

Pipetting errors are detected by: (a) during pipetting, measuring the pressure in the tip of a pipetting device and determining an earlier rate of change of the pressure in the tip; (b) based on the earlier rate of pressure change and a previous pressure value $p_i$, determining an expectation range for the pressure $p_{i+1}$ at a further moment in time and/or an expectation range for the rate of pressure change $\delta_{i+1}$ based on the pressure at the further moment in time $t_{i+1}$; (c) at the further moment in time $t_{i+1}$ measuring the pressure $p_{i+1}$ in the tip; and (d) determining the occurrence of a pipetting error by comparing the measured pressure $p_{i+1}$ at the further moment $t_{i+1}$ in time and/or a rate of pressure change $\delta_{i+1}$ calculated on the basis of the pressure $p_{i+1}$ at the further moment $t_{i+1}$ in time.

19 Claims, 5 Drawing Sheets

(56) References Cited

U.S. PATENT DOCUMENTS

| | | | |
|---|---|---|---|
| 6,121,049 A * | 9/2000 | Dorenkott et al. | 436/50 |
| 6,370,942 B1 * | 4/2002 | Dunfee et al. | 73/37 |
| 7,270,013 B2 * | 9/2007 | Bhullar et al. | 73/861 |
| 8,307,722 B2 * | 11/2012 | Tajima et al. | 73/864.11 |
| 8,475,740 B2 * | 7/2013 | Watanabe et al. | 422/521 |
| 2009/0070049 A1 * | 3/2009 | Ziegler et al. | 702/50 |

* cited by examiner

METHOD, COMPUTER PROGRAM, AND APPARATUS FOR DETECTING PIPETTING ERRORS

RELATED APPLICATIONS

This application is a 35 USC 371 national phase application of PCT/EP2010/064235, filed Sep. 27, 2010, which claims the benefit of priority to European Application No. 09171349.5, filed Sep. 25, 2009, the contents of which are hereby incorporated by reference as if recited in full herein.

BACKGROUND OF THE INVENTION

One of the instruments used in laboratories for acquiring a predetermined volume of a fluid is a pipet. For automated procedures a fluid is aspirated by the movement of a piston and no visual or other acknowledgement of the aspirated volume is obtained.

Due to several causes, the actually aspirated and/or dispensed volume does not always match the intended aspirated volume. Possible causes are:
  the aspiration of particulate objects like blood clots fully, or partly blocking the tip's orifice during the full aspiration period or a fraction thereof,
  a too small a volume in the container where the fluid is to be aspirated from; or
  the aspiration of foam that may be present on top of the fluid in the container where the fluid is aspirated from.

Techniques have been developed to detect possible conditions that may indicate deviations of the aspirated volume. In one such technique, the pipet is provided with a pressure sensor in or close to the tip of the pipet. The fluid is aspirated a first time and the pressure transient p(t) in the pipet is measured during aspiration. If the aspirated volume is correct, a pressure profile has been obtained that reflects a correct aspiration. This profile is then stored for later use. During subsequent aspirations of other fluids and using other tips, the corresponding pressure transient in the, possibly other, tip is measured and—after some form of data processing—compared to the profile of the first run. As long as the pressure stays within a predetermined bandwidth of the profile of the first run, the aspirated volume is assumed to be within an acceptable tolerance of the intended volume.

Drawback of this technique is that due to differences in for example the diameter of the orifice of the tip, variations of the pressure profiles are possible, depending on the specific pipet tip used and on the varying fluid properties, causing the acceptance bandwidth to be broad and the method to be insensitive.

BRIEF SUMMARY

An object of the present invention is to provide a more reliable way of establishing the correctness of the aspirated or dispensed volume in for example automated pipetters.

The present invention attains this object by providing a method for detecting pipetting errors comprising the steps of: during pipetting, measuring the pressure in the tip of a pipetting device and determining an earlier rate of change of the pressure $\delta_0$ in the tip; based on the earlier rate of pressure change $\delta_0$ and a previous pressure $p_i$, determining an expectation range for the pressure $p_{i+1}$ at a further moment in time and/or an expectation range for the rate of pressure change $\delta_{i+1}$ based on the pressure at the further moment in time $t_{i+1}$; at the further moment in time $t_{n+1}$ measuring the pressure $p_{i+1}$ in the tip; determining the occurrence of a pipetting error by comparing the measured pressure $p_{i+1}$ at the further moment $t_{i+1}$ in time and/or a rate of pressure change $\delta_{i+1}$ calculated on the basis of the pressure $p_{i+1}$ at the further moment $t_{i+1}$ in time, with respectively the determined expectation range of acceptable pressures and the determined expectation range of acceptable rates of pressure change.

The present invention relates to a method for detecting pipetting errors.

The invention also relates to a computer program for detecting pipetting errors.

The present invention further relates to data carrier for such a computer program.

Furthermore, the invention relates to an apparatus for detecting pipetting errors.

The invention further relates to a system for detecting pipetting errors.

BRIEF DESCRIPTION OF THE DRAWINGS

Further advantages and embodiments will be described by means of the accompanying drawings, wherein.

DETAILED DESCRIPTION

It should be noted here that the word further in "a further moment in time" in this context is relative to the "previous moment" and not to the moment the step is actually performed.

Although this description primarily refers to the aspiration of a fluid, the invention is also applicable to the dispensing of a fluid, as the dispensing of a fluid is mainly the reverse process of the aspiration of a fluid. Therefore, wherever the words aspiration or aspirate are used in this description, the words dispensing respectively dispense should be read too.

Figure 1:
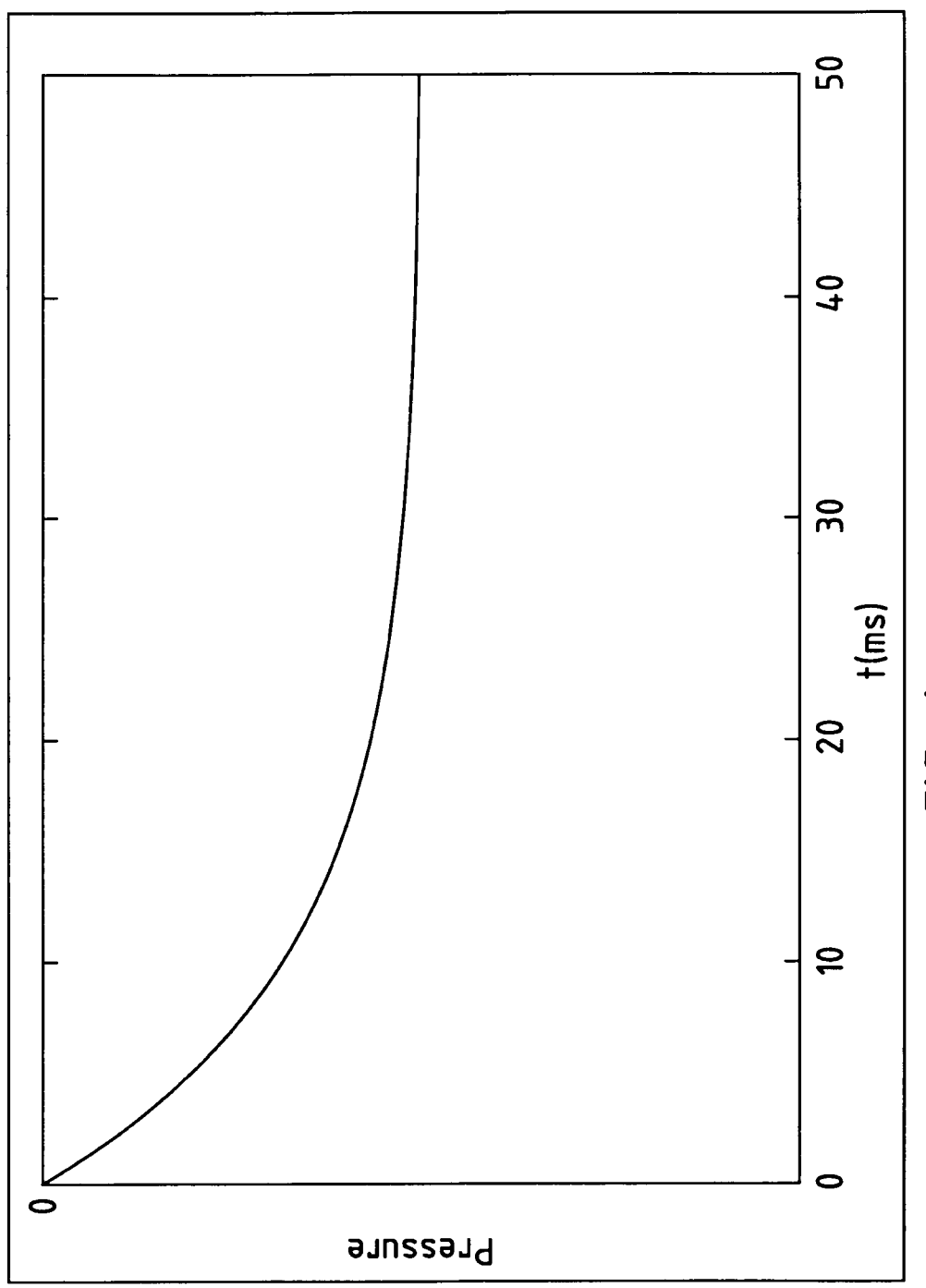
FIG. 1 shows a generic pressure profile of an aspiration by a pipetting device suitable for the method according to the present invention.
Figure 2:
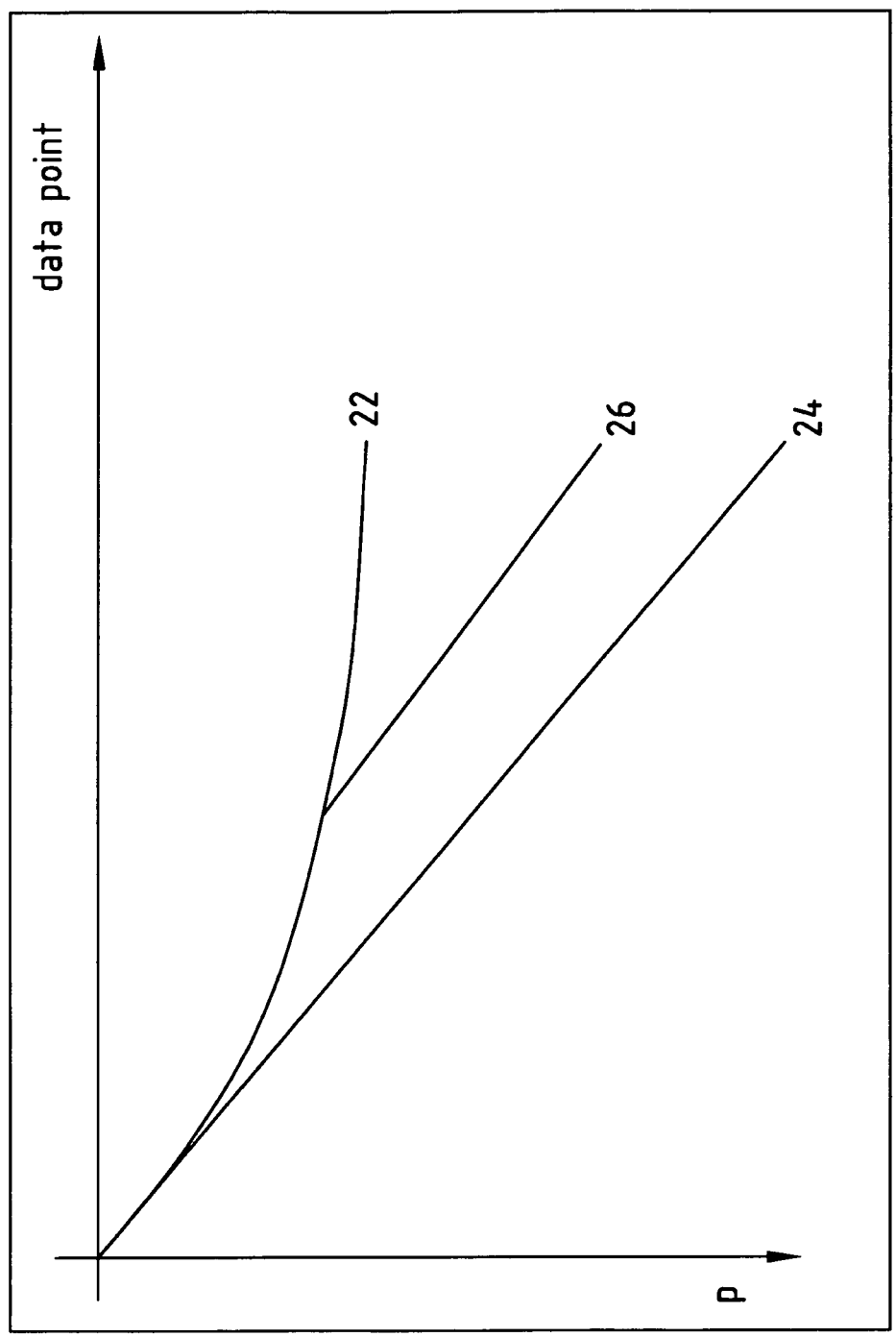
FIG. 2 shows a pressure profile for a pipetting error, namely a clot blocking the orifice, that can be detected by the method according to the present invention.

When the piston is moved at a constant speed during aspiration of the fluid, the pressure 12 (FIG. 1) in the tip (being negative during aspiration) decreases exponentially with the piston position and also with time if the piston moves at a constant speed. However, if a clot is present at the tip during the aspiration the pressure in the tip is characterised by a change linearly proportional to the change in time resp. in position of the piston. With a piston moving at a constant speed, the pressure 24 (FIG. 2) in the tip would be decreasing at a constant rate. If the clot is present at the tip from the start of aspiration until the end, the pressure 24 in the tip will be linearly decreasing from the start until the end of the aspiration. If the clot gets stuck later during the aspiration though, the pressure profile will first show an exponential decrease. From the moment the clot gets stuck, the remainder of the pressure profile 26 will show a linear decrease.

As mentioned before, the invention not only applies to the aspiration of a fluid, but also to the dispensing of a fluid. In the latter case, the sign of the pressures and the pressure change rates is the opposite of the signs in the former case. As only the signs are different, the same principles apply to both aspiration and dispensing.

Figure 3:
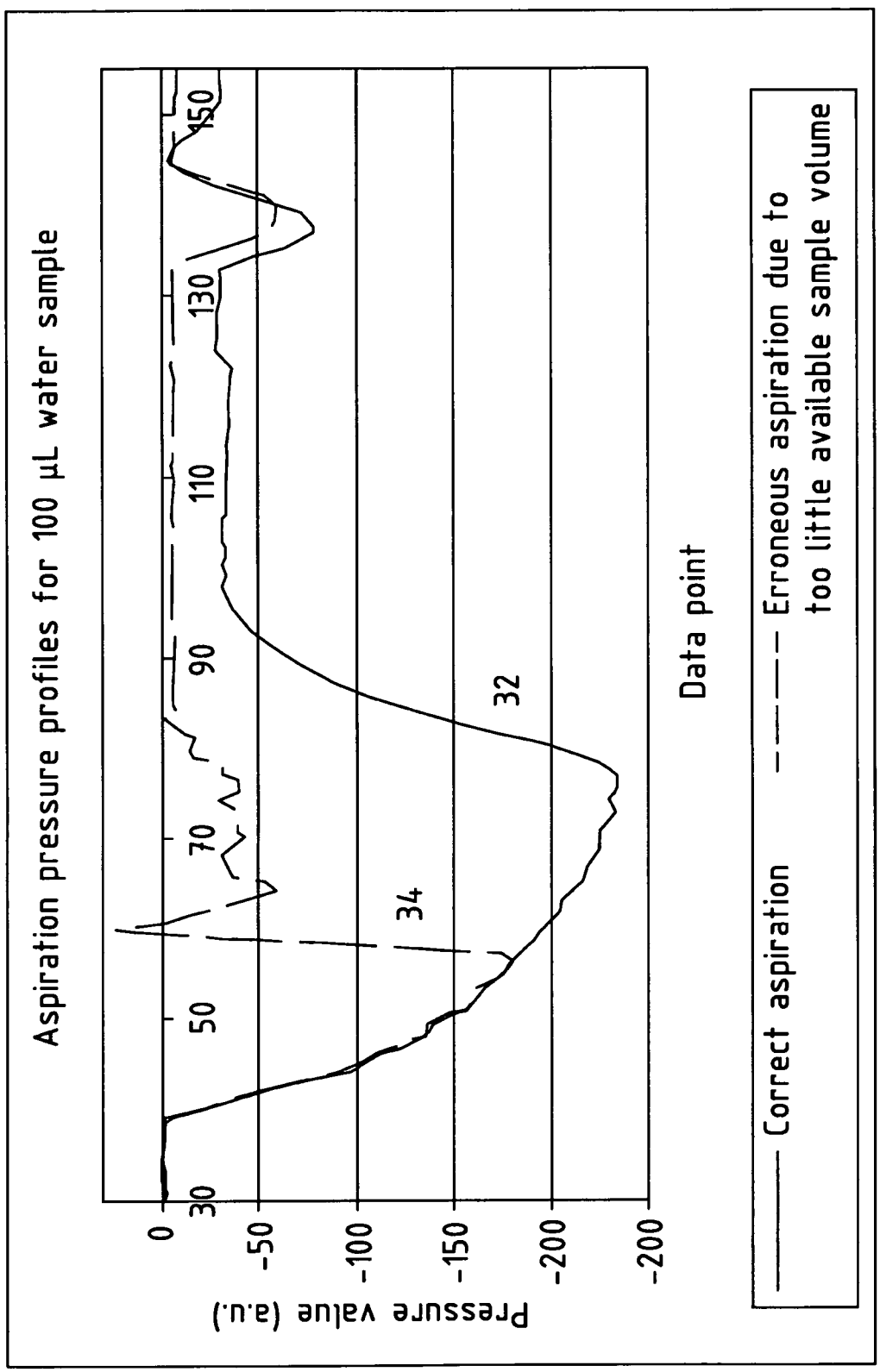
FIG. 3 shows a measured pressure for another pipetting error, namely the aspiration of foam, that can be detected by the method according to the present invention.

Alternatively, if at some point in time, foam is aspirated instead of the fluid, or if the volume of the fluid to be aspirated appears to be insufficient during aspiration, the pressure in the tip rapidly increases (graph 34, FIG. 3), to a value sometimes even close to the ambient pressure.

By determining a rate of change of the pressure in the tip and at a later moment during pipetting determining the pressure and/or the rate of change of pressure and determining whether the pressure and/or the rate of change of pressure is to be expected based on the earlier rate of change of the pressure, the presence of a pipetting error is determined.

Most of the time it is desirable to monitor for pipetting errors over the full course of the pipetting operation. Therefore, in a preferred embodiment the earlier rate of pressure change $\delta_0$ is initially determined at or shortly after the start of pipetting. In one embodiment, subsequent pressures and/or rates of pressure changes are compared against this initial rate of pressure change. In alternative embodiments, the earlier rate of pressure change $\delta_0$ is determined repetitively, and multiple earlier rates of pressure change $\delta_{0,i}$ are determined that each serve as a local reference, whereas the earlier rate of pressure change $\delta_0$ serves as a single global reference.

A clear advantage of this method is the lack of a need for doing a separate calibration run to determine the pressure profile and the method being insensitive to variability of different tips and/or fluids: the calibration of the pressure profile and of its dependency of materials used, is an intrinsic part of the total profile. Right from the start, the pressure profile is monitored and pipetting errors can be detected at the first run already.

In a further aspect of the invention, a method is provided, wherein the step of determining the earlier rate of pressure change $\delta_0$ comprises: measuring the pressure at at least two moments in time; and determining the pressure change between the two moments in time. If the pressure profile is sampled at a fixed sample rate, the rate of change of pressure can easily be expressed as an absolute change per sample. If a variable sample rate is used, it is preferable to express the rate as a change per time unit. If one rather samples as a function of the piston position it can be expressed as change per unit volume or stepper motor step.

In another aspect of the invention, a method is provided, wherein a lower bound of the expectation range of acceptable pressures is set to a value higher than the pressure that would have been obtained at the further moment if the pressure would have constantly decreased at said earlier rate of change $\delta_0$ over the time period from the measuring of the pressure for determining the earlier rate of change $\delta_0$ until the further moment. As stated earlier, if a clot is present at the tip orifice, the pressure decreases at a constant rate. As long as the pressure drop since the moment the earlier rate of change $\delta_0$ has been determined is less than the pressure drop that would have occurred if the rate of change would have been constant, namely $\delta_0$, it can be assumed that no clot is present.

In again another aspect of the invention, a method is provided, wherein an upper and/or lower bound of the expectation of acceptable pressures is set to the pressure $p_i$ at the previous moment $t_i$ and offset by a value proportional to the product of the earlier rate of change $\delta_0$ and the time lapsed between the previous moment in time $t_i$ and the further moment in time $t_{i+1}$.

The upper and lower bounds define a range. The range provides some robustness to noise present in the pressure signal. The noise may be measurement related, such as noise induced in the pressure sensor, but may also be caused by variations in the plunger speed when a stepper motor is used to drive it. The amount of noise determines how the offsets should be chosen. The less noise in the system, the smaller the offsets can be chosen, and the more accurate the detection of pipetting errors will be.

In a further aspect according to the present invention, a method is provided, wherein the proportionality of the offset is defined by a preset factor 2 for the upper bound.

In an alternative aspect of the invention, a method is provided, wherein the proportionality of the offset is defined by a preset factor 1 for the upper bound. Although the pressure is theoretically expected to be strictly continuously decreasing, the presence of noise may (in a noisy system) cause a positive contribution to the pressure signal that exceeds the negative pressure change due to the progress of the pipetting process, resulting in an increase in pressure. Therefore, depending on the amount of noise present in the system, a (slight) pressure increase may be acceptable.

During a correct aspiration, the pressure is expected to decrease continuously while the rate of decrease diminishes. The pressure decrease should however not turn into an increase. If such an increase is detected, it is likely that either foam is aspirated, or the volume present in the container where the fluid is aspirated from is insufficient, and the tip of the pipet is no longer submerged in the fluid. In order to allow for some noise in the measured pressure, especially at the end of the aspiration when the pressure decrease is small, it is preferred to allow for a small increase in pressure. Despite the allowance of (small) increases of the pressure, the chance of getting false positives is small, as the aspiration of foam or the insufficiency of the volume in the container aspirated from normally results in a large increase of the pressure.

According to another aspect of the invention, a method is provided, wherein the proportionality of the offset is defined by a preset factor −4 for the lower bound.

According to an alternative aspect, the invention provides a method, wherein the proportionality of the offset is defined by a preset factor −3 for the lower bound.

If different criteria are used for determining the upper and lower bounds, it should be noted that for dispensing, the upper and lower bounds are swapped compared to aspiration as the pressure profile is mirrored in the horizontal axis. (The only difference between aspiration and dispensing is the change of signs of the pressures.)

In another aspect of the invention, a method is provided, wherein an upper and/or lower bound of the expectation of acceptable pressures is set to the pressure $p_i$ at the previous moment $t_i$ and offset by a value proportional to the product of the rate of change $\delta_i$ at the previous moment in time $t_i$ and the time lapsed between the previous moment in time $t_i$ and the further moment in time $t_{i+1}$.

By calculating the rate of pressure change $\delta_i$ at a moment $t_i$, a local reference is used for each determination at time $t_{i+1}$ whether a pipetting error has occurred. Alternatively, a reference rate of pressure change $\delta_i$ can be reused for one or more moments $t_{i+1}$ to determine the occurrence of a pipetting error. In one particular embodiment, a single reference rate of pressure change $\delta_0$ is determined at the start of the pipetting and is used as a global reference in the determination of pipetting errors.

In a preferred embodiment according to the invention, a computer program for detecting pipetting errors is provided, which, when run on a processor, performs the steps of the above method. In one embodiment, the computer program is an application that is executable on a general purpose computer. In another embodiment, the computer program is comprised in the firmware of a dedicated device for laboratory measurements. In an alternative embodiment, the method is hardwired into a circuit comprised in a dedicated device for laboratory measurements.

The present invention also provides a data carrier comprising the above computer program.

In another embodiment, the invention provides an apparatus for detecting pipetting errors, comprising input means for connecting to a pressure sensor, and wherein the apparatus is configured to perform any of the above methods.

In again another embodiment, a system is provided for detecting pipetting errors comprising: a pipetting device, a pressure sensor provided in the pipetting device for measuring the pressure in the tip of the pipetting device, and the above apparatus connected to the pressure sensor.

All of the above mentioned methods and embodiments, are based on determining an expected next pressure value or expected next pressure change, setting a range of acceptable values around the respectively expected next pressure value and expected next pressure change, and determining whether the next measured pressure value or next measured pressure change falls within the range of acceptable values. Alternatively, the aspiration of foam can also be detected by not using the pressure or the pressure change directly, but a metric derived from the measured pressure. An advantageous metric is the ratio between the moving integral of the pressure value and the length of pressure-time curve over the time range used for the moving integral. When foam is aspirated, the pressure dramatically increases quickly to a value close to zero. The moving integral will dramatically decrease, while the length of the pressure-time curve will dramatically increase due to the large pressure change in a small amount of time. Similar to the embodiments and methods described above, an expected value for the ratio of the moving integral and the length of the pressure-time curve is determined. Furthermore, a range of acceptable values around the expected value is determined. When the next measurement is available, an updated ratio of the moving integral and the length of the pressure-time curve is determined and the updated ratio is compared to the range of acceptable values. If the updated ratio is outside the range of acceptable values, foam has been aspired.

A further alternative does not calculate an expected value, but only detects whether the change of the derivative of the ratio of the moving integral and the length of the pressure-time curve exceeds a predetermined threshold. In one specific alternative embodiment use is made of the fact that the presence of foam will cause the pressure to get close to zero, resulting in the moving integral to decrease. The derivative of the moving integral will therefore change sign. By detecting a change of sign in the derivative of the ratio of the moving integral and the length of the pressure-time curve, the aspiration of foam is detected.

The present invention is based on the insight that a correct pressure profile (id est without pipetting errors) should show a strictly decreasing curve 12 (FIG. 1), with a first derivative that is negative and strictly increasing (ultimately approaching zero). Furthermore, the presence of a clot should show up as a strictly decreasing curve 24 (FIG. 2) with a constant negative first derivative. The aspiration of foam or an insufficient volume of fluid to be aspirated will result in a sharp increase in pressure 34 (FIG. 3), even tending towards zero (the reference pressure being the ambient pressure).

Figure 4:
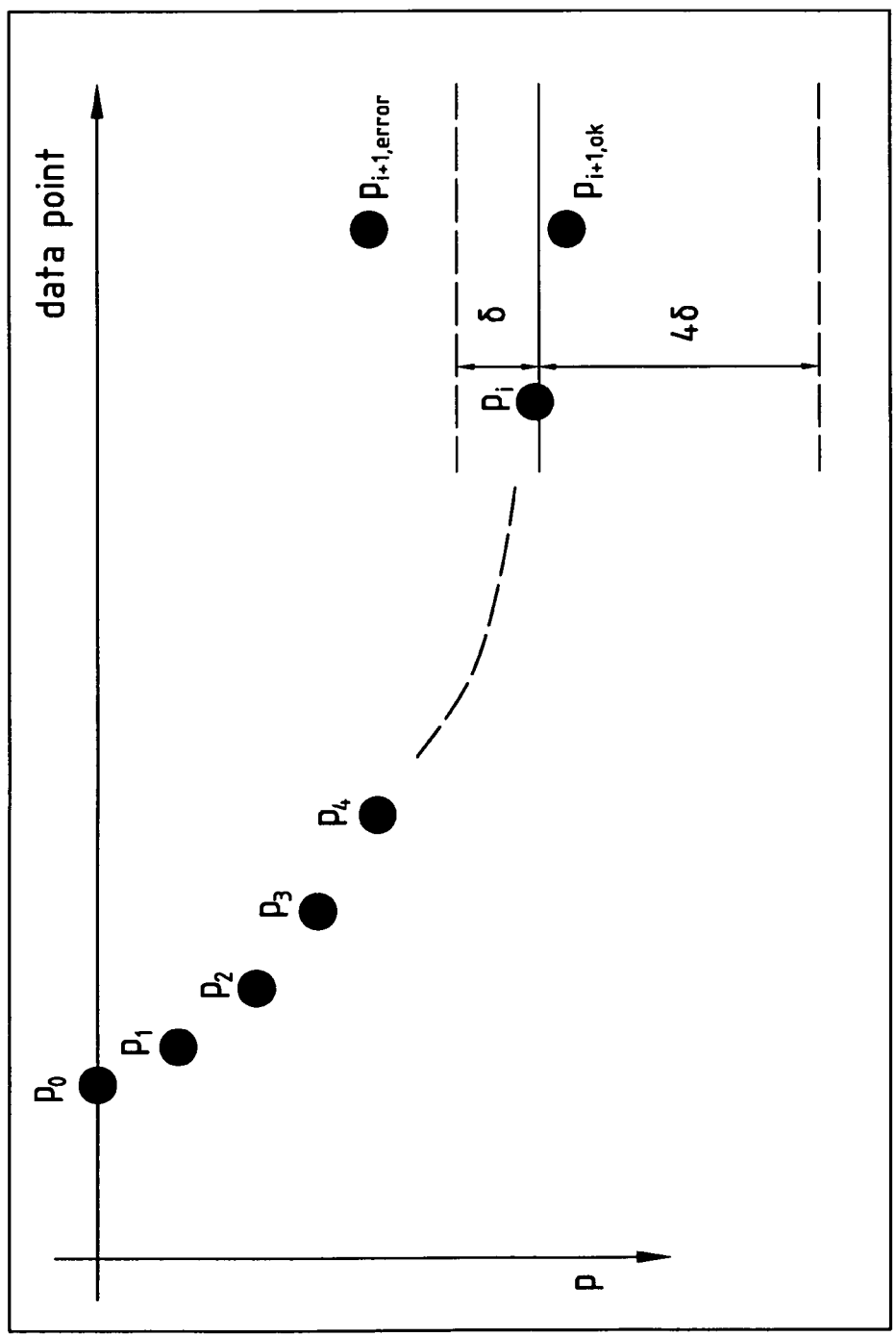
FIG. 4 shows the application of a method according to the present invention to a set of measured pressure datapoints.

An implementation of the method according to the present invention is illustrated by an example in FIG. 4. The method starts taking measurements of the pressure in the tip $p_0 \ldots p_i$ at a fixed sample rate. As soon as five datapoints $p_0 \ldots p_4$ have been acquired the initial earlier rate of pressure change $\delta_0$ is determined over the elapsed time by calculating the difference between the last datapoint $p_4$ and the first datapoint $p_0$, and dividing the difference by the number of sample periods that have lapsed:

$$\delta_0 = \frac{p_4 - p_0}{4}$$

The measuring of the pressure $p_i$ in the tip continues at the fixed sampling rate. For each new measurement $p_{i+1}$ it is determined whether the measured value falls within a bandwidth of allowable pressures around the value of the previous measurement $p_i$. The bandwidth is determined by an upper bound that is set equal to $\delta_0$ above the previous measurement $p_i$, and a lower bound that is set to $4\delta_0$ below pi. If the new measurement $p_{i+1,ok}$ lies within this interval/range, it is assumed that no pipetting error has occurred at this moment $t_{i+1}$. If the new measurement $p_{i+1,error}$ lies outside this expectation, it is assumed that a pipetting error has occurred. If the new measurement lies above the upper bound $p_i + \delta_0$, it is assumed that foam is being aspirated, or that the volume of the fluid in the container wherefrom the fluid is aspirated, is insufficient. If the new measurement lies below the lower bound $p_i + 4\delta_0$, it is assumed that a clot blocks the tip orifice.

Figure 5:
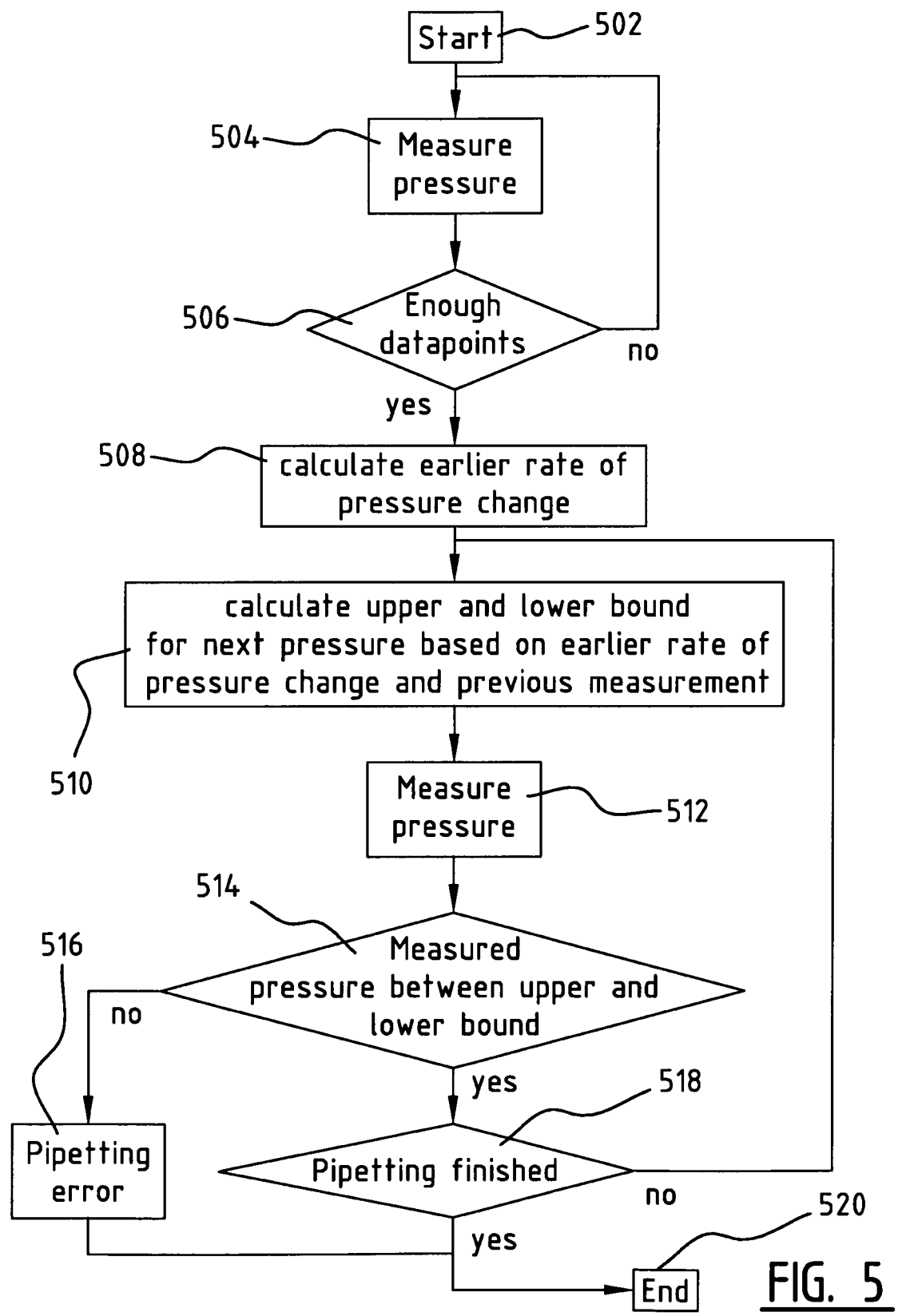
FIG. 5 shows a flow diagram of a method according to the present invention.

FIG. 5 shows a flow diagram of another implementation of a method according to the present invention. Execution starts at the start 502. The pressure is measured 504. Next it is determined 506 if enough datapoints $p_i$ have been acquired to calculate the earlier rate of pressure change $\delta_i$. If not, the next datapoint is acquired 504. As soon as enough datapoints have been acquired to determine the earlier rate of pressure change $\delta_i$, the rate is actually calculated 508. Based on the calculated rate of pressure change $\delta_i$ and the previous pressure $p_i$ an upper and lower bound are calculated 510 for the next measurement $p_{i+1}$. After the next pressure $p_{i+1}$ has been measured 512, a determination is made 514 whether the next measurement $p_{i+1}$ lies between the upper and lower bounds. If not, a pipetting error has been determined 516. If the next measurement $p_{i+1}$ does lie between the upper and lower bounds, it is determined 518 whether pipetting has finished. If not, the sequence continues with calculating 510 again new upper and lower bounds. If pipetting has finished, the sequence ends 520.

The method shown in FIG. 5 uses an initial earlier rate of pressure change $\delta_0$ as a global reference value (global with regard to the whole duration of one aspiration) for determining for each further measured pressure $p_{i+1}$ of this aspiration sequence whether a pipetting error has occurred. Alternatively, an earlier rate of pressure change $\delta_i$ can be calculated repeatedly based on recent measurements, instead of initial measurements. This way, further measured pressures $p_{i+1}$ are evaluated based on a local reference. For this alternative method, the flow chart of FIG. 5 needs only a single change. The no-branch from step 518 to above step 510, should now end above step 508, the calculation of the earlier rate of pressure change, instead of ending above step 510.

The aforementioned embodiments are only presented as mere examples of embodiments according to the invention. The person skilled in the art will understand that adaptations and modifications of the presented embodiments are possible within the scope of the invention. It is for example possible to combine two or more of the embodiments to obtain another (not illustrated) embodiment according to the invention. The scope of the protection sought is therefore defined by the following claims.

The invention claimed is:

1. Method for detecting pipetting errors comprising the steps of:
   aspirating or dispensing a predetermined volume of a fluid using a pipetting device;
   during the aspirating or dispensing, measuring pressure in a tip of the pipetting device and determining an earlier rate of change of pressure in the tip using pressure measurements previously obtained during the same respective aspirating or dispensing;
   based on the earlier rate of pressure change and a pressure $p_i$ that was previously measured during the respective aspirating or dispensing, determining, during the respective aspirating or dispensing, (i) an expectation range for a pressure $p_{i+1}$ in the tip at a further moment in time $t_{i+1}$ and/or (ii) an expectation range for a rate of pressure change $\delta_{i+1}$ based on the pressure $p_{i+1}$ in the tip at the further moment in time $t_{i+1}$;
   at the further moment in time $t_{i+1}$ during the course of the respective aspirating or dispensing, measuring the pressure $p_{i+1}$ in the tip; and
   determining, using a processor, occurrence of a pipetting error by comparing the measured pressure $p_{i+1}$ at the further moment in time $t_{i+1}$ during the respective aspirating or dispensing and/or a rate of pressure change $\delta_{i+1}$ calculated on the basis of the pressure $p_{i+1}$ at the further moment $t_{i+1}$ in time during the respective aspirating or dispensing, with the determined expectation range for the pressure $p_{i+1}$ and/or the determined expectation range for the rate of pressure change $\delta_{i+1}$, respectively.

2. Method according to claim 1, wherein the step of determining the earlier rate of pressure change comprises:
   measuring the pressure in the tip for at least two moments in time; and
   determining the earlier rate of pressure change by calculating a pressure change between the at least two moments in time.

3. Method according to claim 1, wherein a lower bound of the expectation of acceptable pressures is set to a value higher than the pressure that would have been obtained at the further moment in time if the pressure would have constantly decreased at said earlier rate of change over a time period from the measuring of the pressure for determining the earlier rate of change until the further moment.

4. Method according to claim 1, wherein an upper and/or lower bound of the expectation of acceptable pressures is set to the pressure $p_i$ at a previous moment $t_i$ and offset by a value proportional to a product of the earlier rate of pressure change and time lapsed between a previous moment in time $t_i$ and the further moment in time $t_{i+1}$.

5. Method according to claim 4, wherein proportionality of the offset is defined by a preset factor of 2 for the upper bound.

6. Method according to claim 4, wherein proportionality of the offset is defined by a preset factor of 1 for the upper bound.

7. Method according to claim 4, wherein proportionality of the offset is defined by a preset factor of −4 for the lower bound.

8. Method according to claim 4, wherein proportionality of the offset is defined by a preset factor of −3 for the lower bound.

9. Method according to claim 1, wherein an upper and/or lower bound of the determined expectation range for the pressure $p_{i+1}$ is set to the pressure $p_i$ at a previous moment $t_i$ and offset by a value proportional to a product of the rate of change $\delta_i$ at the previous moment in time $t_i$ and time lapsed between the previous moment in time $t_i$ and the further moment in time $t_{i+1}$, wherein proportionality of the offset is defined by a preset factor.

10. Method of claim 1, wherein all of the steps are carried out by a processor.

11. Non-transitory data carrier containing computer instructions stored therein for causing a computer to perform the method of claim 1.

12. Apparatus for detecting pipetting errors, comprising input means for connecting to a pressure sensor, and
   wherein the apparatus is configured to perform the method of claim 1.

13. System for detecting pipetting errors comprising:
   a pipetting device,
   a pressure sensor provided in the pipetting device for measuring the pressure in the tip of the pipetting device, and
   an apparatus according to claim 12 and connected to the pressure sensor.

14. A method for detecting pipetting errors during a pipetting operation, comprising the steps of:
   a) during aspiration or dispensing of a pipetting operation, measuring pressure in a tip of a pipetting device;
   b) determining whether enough pressure datapoints $p_i$ have been acquired during a respective aspiration or dispensing to calculate an earlier rate of pressure change occurring during the same aspiration or dispensing;
   c) if it is determined that not enough pressure data points $p_i$ have been acquired during the same aspiration or dispensing, repeating steps a) and b);
   d) if it is determined that enough pressure data points $p_i$ have been acquired, calculating, for each respective aspiration or dispensing, the earlier rate of pressure change using the measured pressure data points from that respective aspiration or dispensing;
   e) calculating, during each aspiration or dispensing, an upper and lower bound for that aspiration or dispensing, of a next pressure measurement $p_{i+1}$ based on the calculated earlier rate of pressure change and a pressure $p_i$ that was previously measured during that aspiration or dispensing;
   f) during the aspiration or dispensing, measuring a next pressure $p_{i+1}$;
   g) determining whether the next pressure $p_{i+1}$ lies between the calculated upper and lower bounds;
   h) determining, using a processor, that a pipetting error has occurred when the next pressure measurement $p_{i+1}$ does not lie between the upper and lower bounds of step e); and
   i) repeating steps e)-h) for each respective aspiration or dispensing until the aspiration or dispensing of the pipetting operation has finished.

15. The method according to claim 14, wherein step d) is also repeated until the aspiration or dispensing of a respective pipetting operation has finished.

16. The method according to claim 15, wherein the upper and/or lower bound is set to the pressure $p_i$ at a previous moment $t_i$ and offset by a value proportional to a product of a rate of change $\delta_i$ at the previous moment in time $t_i$ and a time lapsed between the previous moment in time $t_i$ and a further moment in time $t_{i+1}$.

17. The method according to claim 14, wherein steps a)-d) are performed during each respective aspiration or dispensing of the pipetting operation, and wherein the upper and/or lower bound is set to the pressure $p_i$ at a previous moment $t_i$ and offset by a value proportional to a product of the earlier rate of change $\delta_0$ and a time lapsed between the previous moment in time $t_i$ and a further moment in time $t_{i+1}$.

18. The method according to claim 14, wherein the pressure in the tip is measured using a fixed sampling rate.

19. A method for detecting pipetting errors during each respective aspiration or dispensing, without requiring a separate calibration run to determine a pressure profile, comprising:
   a) measuring pressure in a tip of a pipetting device;
   b) determining whether enough pressure datapoints $p_i$ have been acquired during a respective aspiration or dispensing to calculate an earlier rate of pressure change occurring during the respective aspiration or dispensing;
   c) if it is determined that not enough pressure data points $p_i$ have been acquired during the respective aspiration or dispensing, repeating steps a) and b);
   d) if it is determined that enough pressure data points $p_i$ have been acquired, calculating, during each respective aspiration or dispensing for that aspiration or dispensing, the earlier rate of pressure change occurring during that respective aspiration or dispensing, using the measured pressure data points obtained during that respective aspiration or dispensing;
   e) calculating, for each respective aspiration or dispensing, using pressure data acquired during that respective aspiration or dispensing, an upper and lower bound for a next pressure measurement $p_{i+1}$ based on the calculated earlier rate of pressure change and a previous pressure $p_i$;
   f) during the respective aspiration or dispensing, measuring a next pressure $p_{i+1}$;
   g) determining during the respective aspiration or dispensing, whether the next pressure $p_{i+1}$ lies between the upper and lower bounds calculated for that respective aspiration or dispensing;
   h) determining, using at least one processor, that a pipetting error has occurred when the next pressure measurement $p_{i+1}$ does not lie between the calculated upper and lower bounds of that respective aspiration or dispensing; and
   i) repeating steps e)-h) until the respective aspiration or dispensing of the pipetting operation has finished.

* * * * *